(12) United States Patent  
Streater (10) Patent No.: US 8,379,228 B1
(45) Date of Patent: Feb. 19, 2013

(54) APPARATUS FOR MEASURING THIN FILM REFRACTIVE INDEX AND THICKNESS WITH A SPECTROPHOTOMETER

(76) Inventor: Alan Douglas Streater, Boulder, CO (US)

( * ) Notice: Subject to any disclaimer, the term of this patent is extended or adjusted under 35 U.S.C. 154(b) by 265 days.

(21) Appl. No.: 12/931,890

(22) Filed: Feb. 14, 2011

Related U.S. Application Data

(60) Provisional application No. 61/338,227, filed on Feb. 16, 2010.

(51) Int. Cl.
*G01B 11/28* (2006.01)
(52) U.S. Cl. ............... 356/630; 356/73; 356/319
(58) Field of Classification Search .......... 356/319–325, 356/630, 73, 135
See application file for complete search history.

(56) References Cited

U.S. PATENT DOCUMENTS

| | | | | |
|---|---|---|---|---|
| 3,477,788 A | * | 11/1969 | Newcomer | 356/332 |
| 3,825,348 A | * | 7/1974 | Nomarski et al. | 356/484 |
| 5,309,212 A | * | 5/1994 | Clark | 356/5.09 |
| 7,233,396 B1 | * | 6/2007 | Hall et al. | 356/369 |
| 7,460,230 B2 | * | 12/2008 | Johs et al. | 356/365 |
| 7,616,319 B1 | * | 11/2009 | Woollam et al. | 356/451 |

* cited by examiner

*Primary Examiner* — Tarifur Chowdhury
*Assistant Examiner* — Michael P Lapage

(57) ABSTRACT

A device is provided that can be inserted into a spectrophotometer, in order to measure the thickness and refractive index of a thin film that is on a sample plate. A pair of identical parallelogram prisms diverts the spectrophotometer beam to measure the attenuated total reflection, and returns an output beam that is in the original beam path, independent of wavelength and rotation angle. The attenuated total reflection of the thin film sample plate is measured in a prism coupling geometry, as a function of wavelength and angle. From this data, combined with normal incidence transmission data, the thickness and refractive index can be extracted.

16 Claims, 4 Drawing Sheets

APPARATUS FOR MEASURING THIN FILM REFRACTIVE INDEX AND THICKNESS WITH A SPECTROPHOTOMETER

CLAIM OF PRIORITY

This patent application claims priority under 35 USC 119 (e)(1) from U.S. Provisional Patent Application Ser. No. 61/338,227 filed Feb. 16, 2010 of common inventorship herewith entitled Apparatus and method for accurately measuring thin film index and thickness with a spectrophotometer.

BACKGROUND OF THE INVENTION

This invention relates to an apparatus and method for measuring the thickness of a thin film layer on a sample plate, and measuring the refractive index of the material of the thin film layer as a function of wavelength.

The optical properties of thin films are often sensitive to the process used for producing the film. For example in thin film deposition the index of refraction is often sensitive to partial pressures of process gases, beam voltages, substrate temperatures, and a host of other parameters, some of which are not even well known or understood. Complex multi-layer thin film designs require accurate knowledge of the optical properties of the individual thin film layers. Manufacturers therefore have a need to accurately measure the optical properties of their thin film layers from a particular process. The properties of special interest are the refractive index and the extinction coefficient (or the real and imaginary parts of the complex index), both of which depend on wavelength. Currently they do this using either an ellipsometer, a prism coupling system, or by a standard method for extracting the parameters from transmission spectra for a single-layer film.

Extracting the index from the transmission spectrum is usually the least expensive method, because thin film manufacturers usually already have a spectrophotometer (or many) for production control of their films. This method has the advantage that it is applicable to all wavelengths accessible to the spectrophotometer, but it has the disadvantage that it is traditionally not very accurate.

Prism couplers and Ellipsometers are quite expensive and are usually more limited in the range of wavelengths over which the index can be measured.

The difficulty with measuring the index of refraction for thin film materials from a transmission scan is that the gross features in the transmission spectrum are largely dependent on only the optical thickness, which is the product of the index and the thickness, but the gross spectral features are not as sensitive to the index and the thickness individually. Thus the optical depth can be determined easily and accurately, but it is difficult to measure the thickness and the index individually. Another way to describe this situation is that a fractional change in the index or thickness has largely the same effect on the spectrum, so it is difficult to determine index and thickness individually when fitting a transmission spectrum to extract these parameters. There are some differences, mainly in the transmission levels, but these are more subtle and difficult to measure accurately.

The situation changes radically when incident angles are beyond the critical angle. Here the phases become a sensitive function of the index. Because the phase changes are sensitive to the index, the gross features of the spectrum now change differently when the index and thickness are changed by the same fractional amount. This is the essential physics involved in using prism coupling to measure the index of refraction.

SUMMARY OF THE INVENTION

This invention is a device that can be inserted into a spectrophotometer, in order to measure the thickness and refractive index of a thin film that is on a sample plate. A pair of identical parallelogram prisms diverts the spectrophotometer beam to measure the attenuated total reflection, and returns an output beam that is in the original beam path. The pair of prisms can be rotated in opposite directions by equal angles, thus preserving a reflection symmetry in the system that assures that the output beam stays in the original beam path, independent of wavelength and rotational angle. The attenuated total reflection of the thin film sample plate is measured in a prism coupling geometry, as a function of wavelength and angle. From this data the thickness and refractive index can be extracted using standard theoretical optimization methods.

Some embodiments include polarizers for spectrophotometers that are not already polarized. Other embodiments are described that include apertures and a retro-reflection measurement system to improve the accuracy of the device.

BRIEF DESCRIPTION OF THE DRAWINGS

Embodiments will now be described with reference to the accompanying simplified, diagrammatic, not-to-scale drawings.

DETAILED DESCRIPTION OF PREFERRED EMBODIMENTS

All terms not defined herein have their common art recognized meanings. To the extent that the following description is of a specific embodiment or a particular use of the invention, it is intended to be illustrative only, and not limiting of what is claimed. Immaterial modifications to what is described may be made without departing from what is claimed.

For all embodiments described here and in the claims, we refer to a first wavelength band, which is the wavelength range for operation of the device.

In all embodiments described here, a spectrophotometer consists of a light source that produces light over a range of wavelengths, a wavelength selection mechanism, a sample area, and a detector or array of detectors. The wavelength selection mechanism selects light from the light source that is also within a second wavelength band that represents the resolution of the spectrometer. The second wavelength band has a central wavelength and a resolution width, and more generally a spectral resolution function that is the intensity spectrum that the apparatus would measure if the source produces only a single wavelength of light. The light from the light source follows a spectrophotometer beam path with a central axis. The spectrophotometer beam path passes through the sample area. A sample or a more complex measurement apparatus can be placed in the spectrophotometer beam path in the sample area, for a measurement of the light intensity that emerges from the sample or more complex measurement apparatus, in a beam that is in the same line as the spectrophotometer beam path in the sample area. The wavelength selection mechanism can be modified (usually by mechanical rotation) so that the second wavelength band changes, usually in central wavelength, but also possibly in the width or in other aspects of the spectral resolution function. In the case of a detector array, each detector in the array senses electromagnetic radiation with wavelength within a second wavelength band for that detector. A spectrophotometer also refers to a Fourier Transform Spectrometer, which consists of a light source and a scanning interferometer. Here a signal is recorded as a function of the optical path length that is scanned, and the wavelength selection mechanism includes a mathematical operation that involves the Fourier transform of the signal.

The measurement apparatus described herein is a particular complex apparatus that can be inserted in the beam path of a spectrophotometer. The apparatus has an input beam path and an output beam path that are in-line, so that it can be used in all spectrophotometers without modification of the spectrophotometer.

Figure 1:
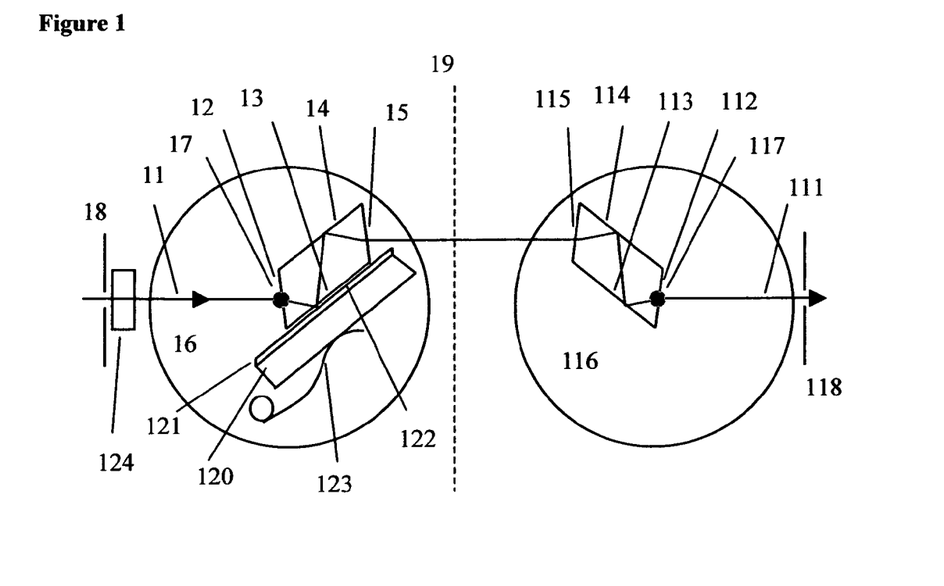
FIG. 1 shows a schematic representation of an embodiment of a device for measuring in a spectrophotometer, the thickness and refractive index of a thin film layer that is on a thin film sample plate.

A first embodiment of a device for measuring the refractive index and thickness of a thin film that is applied to a sample plate is shown schematically in FIG. 1.

An input beam path 11 represents a path that electromagnetic radiation of a central wavelength and direction enters the device. The beam path has the form of a line in space with a direction.

A first right prism consists of material that has a refractive index and that is transparent in the first wavelength band, and has a refractive index $n_p$. The first right prism has at least four surfaces with normals that all lie in a plane, which in the claims we list as:

A first planar first transmission surface 12

A first planar first reflection surface 13, which forms an acute angle with the first planar first transmission surface that we call the first prism angle A first planar second transmission surface 14, that is parallel to the first planar first transmission surface A first planar second reflection surface 15, that is parallel to the first planar first reflection surface.

A second right prism is identical to the first right prism, and therefore also has at least four corresponding surfaces with normals that all lie in a plane, which in the claims we list as:

A second planar first transmission surface 112

A second planar first reflection surface 113

A second planar second transmission surface 114

A second planar second reflection surface 115

The four planar surfaces 12, 13, 14, 15, 112, 113, 114, 115 are polished to an optical polish that is common for optical components.

The first right prism is mounted onto a first rotation stage 16. The first rotation stage has a first rotation axis 17, and the means to select a first rotational position (angle) about the first rotation axis. The first rotation axis lies in the first planar first transmission surface. This axis is also parallel to a line in each of the other surfaces mentioned, which is another way of saying that the normal of all of the surfaces lie in a plane (the plane of the paper in FIG. 1). This is also a statement that the first right prism is indeed a right prism with regard to the four surfaces listed.

The second right prism is mounted onto a second rotation stage. The second rotation stage has a second rotation axis 117 and the means to select a second rotational position about the second rotation axis. The second rotation axis lies in the second planar second transmission surface, and is also parallel to the first rotation axis 17. The second right prism, being identical to the first right prism, is also a right prism with regard to the four surfaces listed. These conditions assure that the normals for the surfaces listed above for the second right prism are in the same plane as the normals for the surfaces listed above for the first right prism, which in turn assures that the light beam remains in a single plane as it passes through the system.

The first rotation stage is positioned so that a light beam propagating with a central input axis is aligned and in the direction of the input beam path. The light beam enters into the first right prism through the first planar first transmission surface. The beam direction may change due to Snell's law, and can be slightly different for different wavelengths, due to the dispersion in the prism material. The light beam then is incident on the first planar first reflection surface 13, at an angle of incidence to the first reflection surface, $\theta$, that is greater than the critical angle, $\theta_c$, which (assuming that the surrounding medium has index very near 1) is given by $\theta_c = \sin^{-1}(1/n_p)$. When no sample is present, the light reflects due to total internal reflection. The light beam then transverses the prism, and then is incident on a first planar second reflection surface 14, where it also reflects due to total internal reflection.

The light beam then reflects from the first planar second reflection surface, and then exits through the first planar second transmission surface.

Then the light beam enters the second right prism through the second planar second transmission surface. Then the light beam reflects from the second planar second reflection surface and propagates across the prism. Then the light beam reflects from the second planar first reflection surface, and then exits through the second planar first transmission surface in an output beam path that is aligned with the central input axis. This is achieved when the second right prism is mounted upside-down relative the first right prism, with the corresponding surfaces in reflected symmetry about a plane of symmetry 19.

The system also comprises a means for pressing a thin film sample plate into close contact with the first planar first reflection surface 12, the means indicated in FIG. 1 as a spring clip 123. The thin film sample plate is made of a substrate material, with surfaces that are polished, and has a thin film structure on one surface. Typically the thin film structure will be a single layer, with index $n_1$ and thickness $d_1$. Pressing the thin film sample plate against the first planar first reflection surface normally provides a thin gap layer between that layer and the thin film layer, which is the standard prism coupling geometery. If the surfaces are highly polished and the surfaces are too clean, optical contacting may occur, resulting in undesirable sticking and also a gap layer that is too thin for subsequent analysis of the results. If necessary this can be avoided by adding a few particles of fine dust to the surfaces. More pressure can be used if the gap is too thick. Generally the ideal gap size is on the order of the wavelength (or a few wavelengths) of the light. One example embodiment of a means for pressing a thin film sample plate into close contact with the first planar first reflecting surface is a spring clip, as shown in FIG. 1.

The benefit of this geometry is that the output beam path is in-line with the input beam path, independent of wavelength. Thus when the apparatus is placed in a spectrophotometer that has a straight beam path in its sample compartment, all wavelengths in the light beam entering the measurement apparatus will emerge in-line and will therefore reach the detector. A similar geometry is commonly applied to form an in-line, broadband half wave plate using two Fresnel Rhomb prisms. When the first right prism is rotated to a new angle, the second right prism is rotated in the opposite rotational direction in order to maintain the reflection symmetry, and the output beam path is again in-line with the input beam path for all wavelengths. This allows for convenient changes to different angles, so that multiple reflection scans can be collected at different angles.

Some spectrophotometers use light that is not polarized. If this is the case, a polarizer, 124, is required so that the light is polarized, so that the reflections are either transverse electric (S-polarized) or transverse magnetic (P-polarized). The polarizer must also operate over the first wavelength band that represents the operating wavelength range for the measurement apparatus. The polarizer can be placed anywhere in the light beam path, where the light beam path refers to the path of the light beam as it propagates through the system.

Some spectrophotometers use light that has a substantial range of angles around the central angles (cone angle), because the light source is an extended source. This complicates the analysis of the spectrophotometer scan data, and uncertainties in the angular distribution can also increase the uncertainty of the results. These complications and uncertainties can be reduced by adding a first aperture 18 in the input beam path, and a second aperture 118 in the output beam path, which reduce the range of angles of the light beam. In some cases adding one aperture to the system will suffice, but adding two apertures is not much harder and better assures a reduction in the cone angle.

The second right prism is always rotated by angles that are equal in magnitude and opposite in rotational direction to the first right prism, so that reflection symmetry is maintained. Therefore it is desirable that the first rotation stage and the second rotation stage be constrained to rotate together in equal and opposite angles. This can be achieved, for example, by using a gear or a belt. The reading of the angular position of the constrained system should concentrate on the first angular position, because it is more critical for the analysis than the second angular position. A small amount of uncertainty in the second angular position, for example due to imperfectly meshed gearing or a slightly loose belt drive, is then tolerable.

Because the angle of incidence of the light onto the first planar first reflection surface is critical to the accuracy of the measurement, it is important to calibrate the first rotation angle so that the angle of incidence is known accurately. We discuss here two ways to achieve this. The first is by calibrating to a thin film sample of known index. This method is discussed below, after a brief description of the method of use for the device. The second method for calibrating the first rotational angle to the angle of incidence is by adding a retro-reflection system that is similar to the mechanism that is typically used in autocollimators. This device that can be added to the measurement apparatus is shown schematically in FIG. 2.

The goal of calibrating the first rotational position to the angle of incidence of the reflection of the beam on the first planar first reflection surface can be accomplished by determining the first rotational position for which the first planar first transmission surface is perpendicular to the light beam. At this position, the angle of incidence is the angle between the first planar first transmission surface, and the first planar first reflection surface. This angle, which we call the apex angle, $\gamma$, can be measured quite accurately for the first right prism using a standard autocollimator that is commonly used in the industry.

Figure 2:
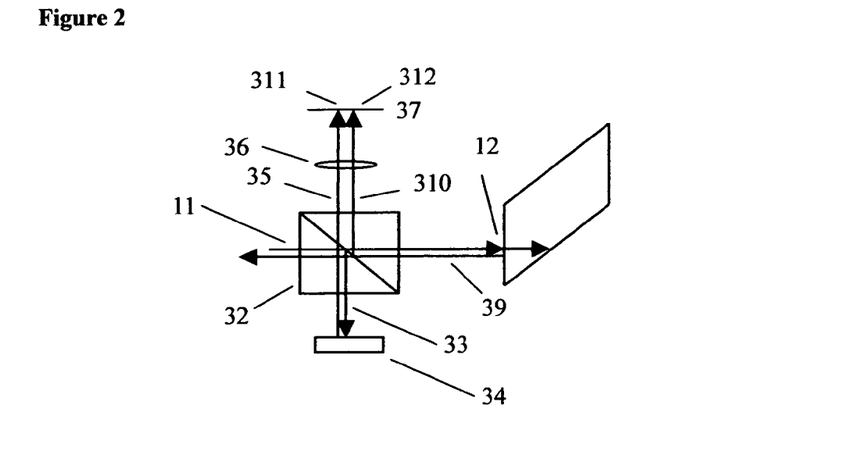
FIG. 2 shows an alignment system that can be added to improve the accuracy of the device shown in FIG. 1.

Indicated in FIG. 2 are the input beam path 11, and the first planar first transmission surface 12. These are the same elements that are indicated in FIG. 1. In addition, the added calibration system comprises a beam splitter 32, a retro-reflector 34, a focusing element 36, and a screen 37. The light beam is reflected by the beam splitter to form a reflected beam 33, that is then reflected by the retro-reflection device to form a retro-reflected beam 35, that returns through the beam splitter, then through the focusing element, and onto the screen, where it forms a first spot 311. Part of the light beam also passes through the beam splitter and is reflected from the first planar first transmission surface to form a first planar first transmission retro-reflected beam 39, that is then reflected by the beam splitter to form a reflected beam of the first planar transmission retro-reflected beam 310, which then passes through the focusing element and onto the screen 37, where it forms a second spot 312. Thus two spots appear on the screen. When the first spot and the second spot overlap in position, the light beam is propagating in a direction that is normal to the first planar first transmission surface, and the angle of incidence of the beam onto the first planar first reflection surface is equal to the apex angle. Autocollimators, which use a similar method, are easily accurate to within a few arc-minutes.

Method of Use for Obtaining Thickness, Refractive Index, and Absorption Coefficient One method for obtaining the thickness of the thin film layer on a thin film sample plate for a specific wavelength for certain situations is described, for example, in R. Ulrich and R. Torge, "Measurement of Thin Film Parameters with a Prism Coupler", Appl. Opt., 12, 2901 (1973). We describe here a somewhat different method that might be more appropriate when reflection data covers a range of wavelengths as well as a range of angles. For descriptive purposes we will assume that the thin film structure consists of a single film layer of thin film material of thickness $d_1$ and refractive index $n_1$, and that the substrate index of the plate is $n_s$.

The geometry of prism coupling can be seen in FIG. 1. The light beam is incident on the first planar first reflection surface 13, and is evanescently coupled through the air gap 122, into the sample thin film layer 121.

The resonant waveguide modes in the thin film sample layer are leaky waveguide modes, so called because the evanescent coupling through the air gap provides a loss mechanism. A leaky mode has a propagation length, which is a characteristic length over which a propagating mode without input excitation will decay, as described for example in Engineering Optics, Springer, 3rd edition, 2009, by K. Iizuka. The propagation length is also sometimes called the coupling length.

There are two cases of interest. The first case, case 1, is when the rays in the sample thin film layer are beyond the critical angle for the interface between the waveguide material and the substrate material of the thin film sample plate. Snell's law can be used to relate the ray directions inside the layer to the direction of the incoming beam, resulting in the condition $n_p \sin(\theta) \geq n_s$ (condition for case 1, no transmission).

Here $n_s$ is the refractive index of the thin film sample plate substrate material. The second case, case 2, is when the above inequality does not hold. In this case light can be transmitted through the sample plate. Here it might be improper to call the structure a waveguide at all, but there is still a resonance, and the there is still an index-dependent phase change at the interface with the air gap, which is the important element for obtaining an accurate measurement of the refractive index.

Case 1 is the more difficult case to treat theoretically, so we start with case 2. For case 2, in which light can be transmitted through the sample plate, the transmission provides an energy loss mechanism. Except in extraordinary circumstances, the propagation length will be much smaller than the beam diameter, and an infinite plane wave solution will be valid, so we can use standard thin film modeling to calculate the reflection and transmission of the system. This theory is described, for example, in Thin-Film Optical Filters, Fourth Edition, Taylor & Francis (CRC Press) (2010), by A. Macleod.

Case 1 is more difficult theoretically because plane wave theory does not apply directly. An infinite plane wave will couple into and out of the waveguide mode periodically, always resulting in 100% reflection. There are several physical effects, however that can reduce the reflection to values that are less than 100%. The first mechanism is loss due to scattering and absorption in the materials, which are greatly enhanced at resonance due to the resonant enhancement of the electric field. This leads to dips at resonance even in the plane wave limit, where the propagation length is much smaller than the beam diameter. If the beam diameter is comparable to the propagation length, then light can couple into the waveguide mode within the beam diameter, and couple back out of the waveguide in a region outside the beam diameter. A dip will then occur if the detector has a limited area. If the detector area is large, the second aperture may be helpful in obtaining a substantial dip. Thus we can still have dips in the reflected signal, even when scattering and absorption are not present. In the case where the coupling is weak, then the resonance wavelength is very close to the resonance wavelength of the guided mode in which no coupling is present. This is the case when the gap size is relatively large, and in this case the propagation length is relatively large. Then a beam diameter that is also relatively large (e.g. 1 mm) will produce a substantial dip. Spectrophotometer diameters are typically rather large anyway. We can also use standard thin film theory to calculate a dip position, by adding a small artificial absorption to provide a loss at resonance wavelength. This will be also in the weak coupling limit, so the calculated resonance wavelength will be accurate when the coupling to the planar waveguide is weak.

In summary, we can use standard thin film theory in all cases, if we introduce a small artificial absorption if the condition for case 1 above is satisfied, and if the coupling is weak, which is almost always the case when a substantial dip is observed for a relatively large beam diameter. This provides a unified theoretical treatment for the reflection spectrum that is valid for a wide range of conditions.

So far the data set consists of a series of reflection scans from the device disclosed here. At each angle we can also record a normalization scan with no sample plate present. Dividing the reflection scans with the part present into the normalization scan, we obtain the fractional reflection data on a scale from 0 to 1. This is standard procedure for using spectrophotometers. We call these normalized scans attenuated total reflections scans, and we call the set of attenuated total reflection scans for various angles the attenuated total reflection data. Now we add to the data set a standard transmission scan of the thin film sample plate at normal incidence (angle of incidence 0). These scans are also normalized by dividing with a scan with no sample present, as is standard for using spectrophotometers. This normal incidence scan can be over a third wavelength band that is wider than the first wavelength band and at least partially contains the first wavelength band.

The transmission scan at normal incidence oscillates in wavelength (or frequency), as the wavelength passes through periods of constructive and destructive interference. The wavelength relative to the optical thickness (product of index and thickness) determines the period of oscillation. Conceptually, the normal-incidence transmission scan provides an accurate measure of the relative dispersion (relative refractive index change from one wavelength to another), since the non-linearity of the optical thickness as a function of wavelength is entirely due to the refractive index dispersion. Thus we can scan the normal incidence transmission over a larger wavelength range (third wavelength band) than the range of the attenuated reflection scans (first wavelength band), so that the accurate values for the relative dispersion over this wider range will be anchored by the accurate absolute values for the refractive index that will come from the attenuated total reflection data. In this way we will obtain accurate index values over the whole larger range. This is helpful when the material of the first right prism and second right prism might has a limited transmission window than the substrate and the film.

The index and thickness of the sample thin film layer can be obtained by a theoretical fit of the thin film theory. The index of refraction of the prism, $n_p$, the index of refraction of the substrate material of the thin film sample plate, $n_s$, the apex angle of the first right prism, $\gamma$, and the first rotational position are known. Unknown parameters that are used to fit the theory to the data set are the sample thin film layer thickness, $d_1$, the air gap thickness $t_g$, the refractive index of the thin film layer, $n_1$, and the absorption coefficient $k_1$. These last two are functions of wavelength. Rather than assigning a different value at each wavelength measured, it is best to us a linear interpolation for these functions, and the knots of the interpolation then become the fitting parameters. This reduces the number of fitting parameters and takes advantage of the inherent smoothness of these functions. In wavelength regions where the functions change more rapidly with wavelength, more knots can be added.

Other experimental realities can be included in the theory. For example, in modeling the transmission scans, the transmission loss at the backside interface of the thin film sample plate can be included in the theory for the normal incidence scan, multiple reflections between the front side thin film structure and the backside interface can be included. Absorption of the substrate material of the thin film sample plate can be included. The theory can be integrated over a spectrometer bandwidth and a range of incoming angles in the beam (cone angle).

A merit function based on the sum of the squares of the difference between the theory and the measurement is appropriate. Regions of data with less noise or more uncertainty can be given less weight. For example, if the substrate material of the thin film sample plate is fused silica, it is appropriate to use less weight for the normal incidence scan in the wavelength region near a water absorption line, where the substrate absorption probably has more uncertainty.

If the method used for depositing the sample thin film has good uniformity, so that the thin film materials that are deposited onto different sample plates of different substrate materials are similar, then we can add attenuated total reflection data and normal incidence scans from the different sample plates together to obtain a larger data set. This larger data set can be fit in the same way.

A similar fitting procedure can be used for calibrating the first angular position to a known angle of incidence, using a thin film sample plate with a known refractive index. A fit is performed, now with the refractive index a fixed input parameter (rather than a fitting parameter), and a first angular position offset is used as a fitting parameter. This first angular position offset corresponds to the first angular position where the angle of incidence is equal to the input apex angle. This is similar in effect to the measurement of the first angular position corresponding to the retro-reflection condition of the beam from the first angular first transmission surface.

Demonstration of the Device and Method of Use

We constructed a demonstration apparatus in which the first right prism was on a rotation stage with 5 arc-minute resolution, while the rotation of the second right prism was done more crudely by attaching it to a block that could rotate by sliding. After setting the first angular position accurately, the second angular position was found by optimizing the absolute transmission through the system. Otherwise the device is as described here, with a polarizer (S-polarization) and apertures. The acute angle of the BK7 prism (apex angle), $\gamma$, is measured to be 54.97 degrees. It was placed in a Perkin Elmer Lambda 900 model spectrophotometer.

We used three sample plates of different substrate materials, all with $Ta_2O_5$ thin film layers that were deposited in the same run by ion beam sputtering. We obtained attenuated total reflection scans over a first wavelength band of 700 nm to 1500 nm, for a fused silica thin film sample plate at a first rotation angle of −0.62 degrees, and for a BK7 thin film sample plate at a first rotation angle of 2.21 degrees. Rotation angles are relative to the first rotation angle that retro-reflects the beam from the first planar first transmitting surface, and positive corresponds to clockwise as shown in FIG. 1. We also measured transmission scans for the same fused silica thin film sample plate, and for another $LiNbO_3$ thin film sample plate. The transmission scan for the fused silica thin film sample plate covered the range 300 nm to 2200 nm. The transmission scan for the $LiNbO_3$ thin film sample plate covered the range 1000 nm to 3000 nm, and the polarization was aligned with the ordinary optical axis. From this data, we obtained the thickness of the thin film samples, the refractive index, and the extinction coefficient, over the range 300 nm to 3000 nm.

Figure 3A:
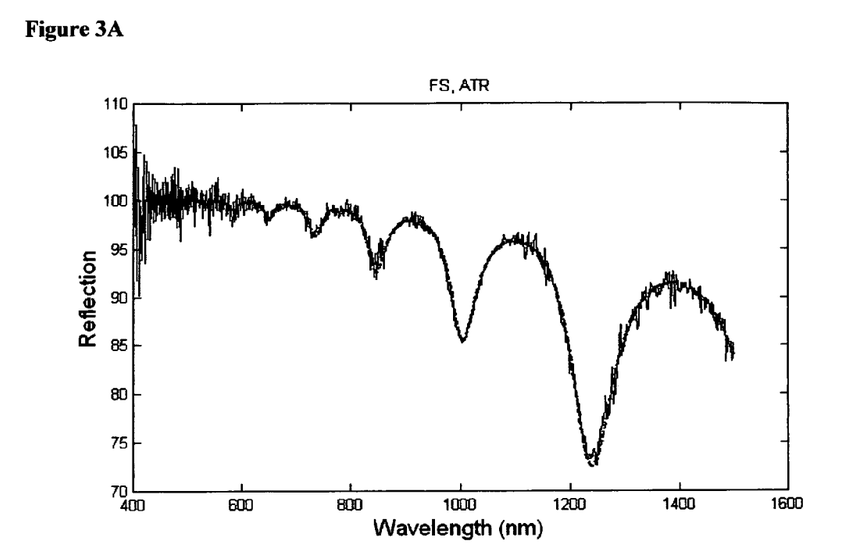
FIG. 3A shows a reflection scan from a spectrophotometer, using the device disclosed (solid line), for a fused silica thin film sample plate with a thin film structure consisting of a single $Ta_2O_5$ layer. A corresponding curve is also shown (dashed line) that is based on a theoretical fit that is used to extract the thickness of the layer, the refractive index of the layer material as a function of wavelength, and the extinction coefficient of the layer material as a function of wavelength.
Figure 3B:
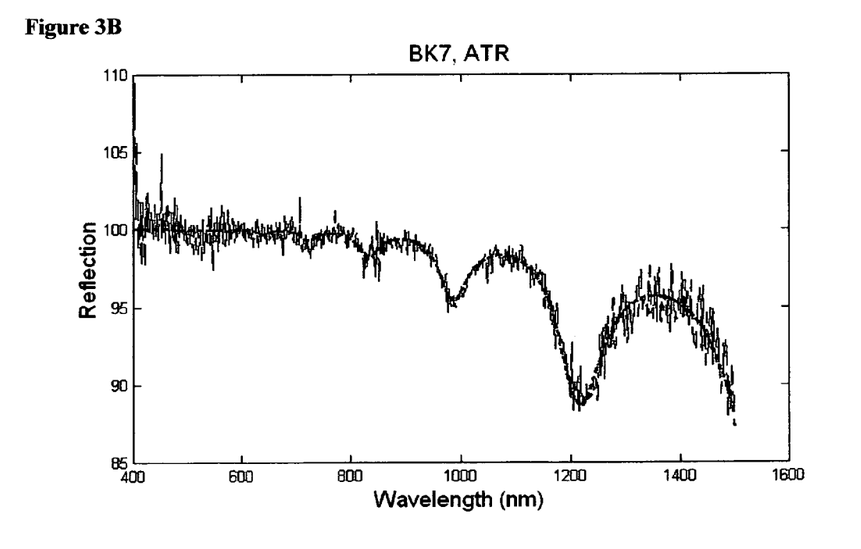
FIG. 3B shows a reflection scan from a spectrophotometer, using the device disclosed (solid line), for a BK7 thin film sample plate with a thin film structure consisting of a single $Ta_2O_5$ layer. A corresponding curve is also shown (dashed line) that is based on a theoretical fit that is used to extract the thickness of the layer, the refractive index of the layer material as a function of wavelength, and the extinction coefficient of the layer material as a function of wavelength.
Figure 4A:
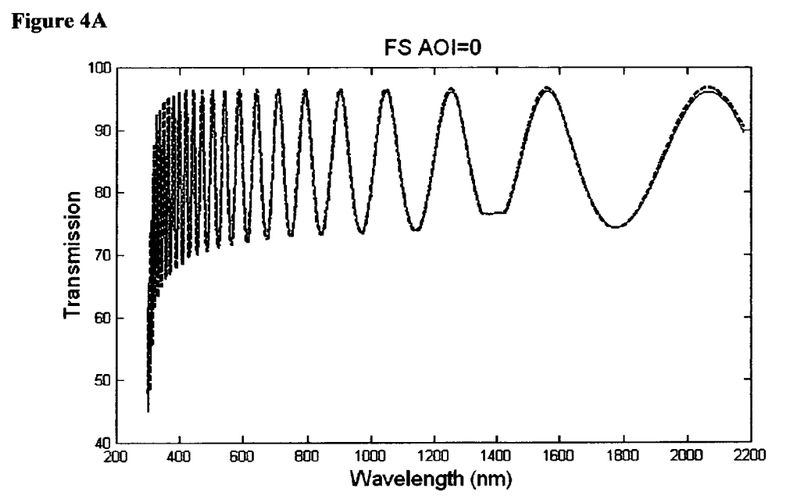
FIG. 4A shows a normal incidence transmission scan from a spectrophotometer, of the fused silica thin film sample plate with a thin film structure consisting of a single $Ta_2O_5$ layer. A corresponding curve is also shown (dashed line) that is based on a theoretical fit that is used to extract the thickness of the layer, the refractive index of the layer material as a function of wavelength, and the extinction coefficient of the layer material as a function of wavelength.
Figure 4B:
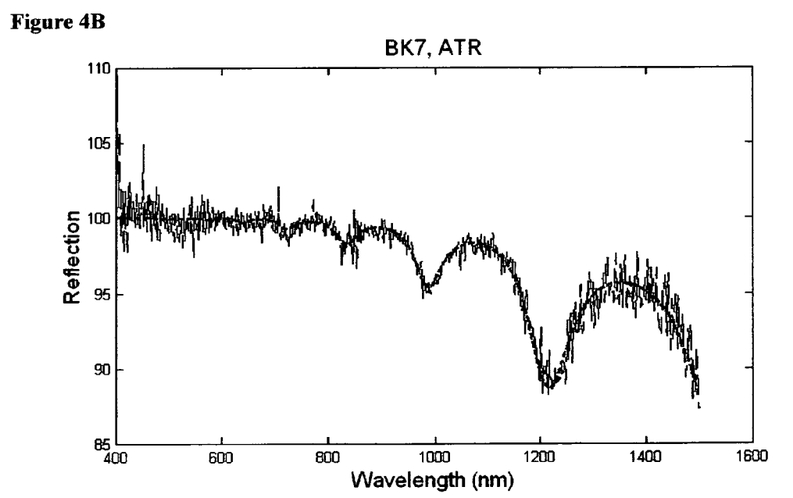
FIG. 4B shows a normal-incidence transmission scan from a spectrophotometer, of a $LiNbO_3$ thin film sample plate with a thin film structure consisting of a single $Ta_2O_5$ layer. The polarization of the spectrophotometer is aligned with the ordinary optic axis of the $LiNbO_3$ substrate material. A corresponding curve is also shown (dashed line) that is based on a theoretical fit that is used to extract the thickness of the layer, the refractive index of the layer material as a function of wavelength, and the extinction coefficient of the layer material as a function of wavelength.

FIG. 3A and FIG. 3B show the attenuated total reflection scans, and the theoretical fits. FIG. 3A is for the fused silica thin film sample plate, and FIG. 3B is for the BK7 thin film sample plate. The corresponding curves for the theoretical fit are also shown as dashed curves in both FIG. 3A and FIG. 3B. FIG. 4A and FIG. 4B show the normal-incidence (0 degree angle of incidence) transmission scans. FIG. 4A is the transmission for the fused silica thin film sample plate, and FIG. 4B is the transmission for the BK7 thin film sample plate. Again, the corresponding curves for the theoretical fit are shown as dashed curves in both FIG. 4A and FIG. 4B. For the normal incidence scan of the fused silica thin film sample plate, there is a region from 1340 nm to 1430 nm where the data was ignored because of uncertainty in the fused silica transmission near the water line.

Figure 5A:
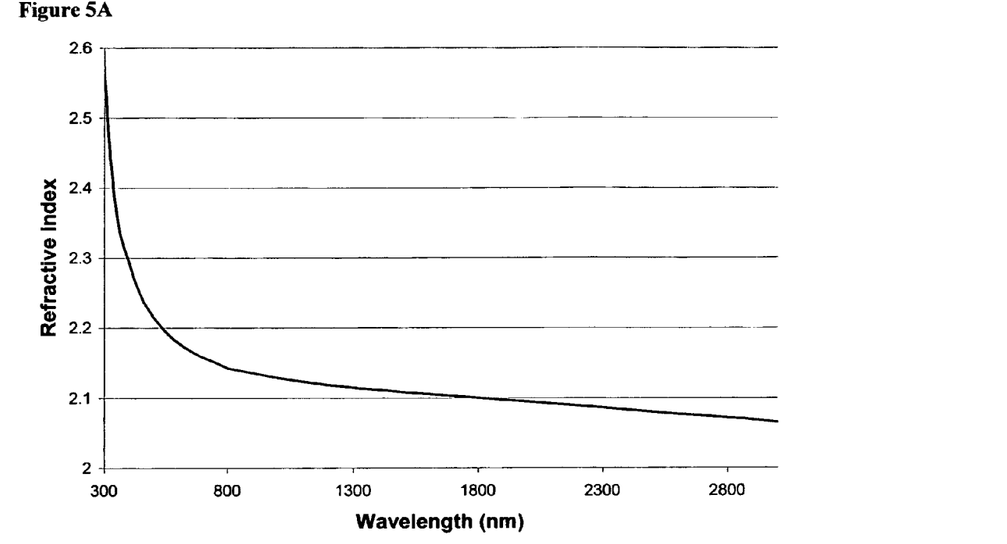
FIG. 5A shows the measured refractive index of the material of the single $Ta_2O_5$ layers on three sample plates, as a function of wavelength.
Figure 5B:
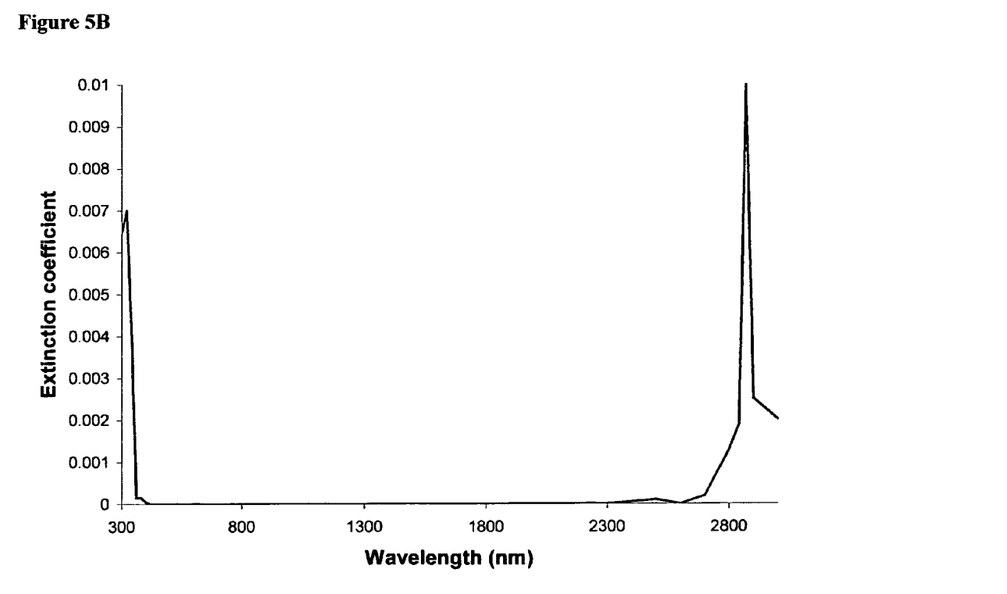
FIG. 5B shows the measured extinction coefficient of the material of the single $Ta_2O_5$ layers on three sample plates, as a function of wavelength.

FIG. 5A shows the extracted refractive index, and FIG. 5B shows the extracted extinction coefficient. The extracted thickness values for the $Ta_2O_5$ layers on the three thin film sample plates were 1479 nm for the fused silica sample plate, 1469 nm for the BK7 plate, and 1494 nm for the $LiNbO_3$ sample plate. The differences in thickness are consistent with typical part-to-part uniformity for the coating chamber.

In this first experiment the accuracy suffered somewhat from an uncertainty in the angle of incidence that was on the order of 15 arc minutes, owing to the difficulty in identifying the first angular position that was precisely normal to the light beam. The more sophisticated auto-collimation system as described in FIG. 2 was not used. The improved measurement of the first rotation angle for retro-reflection, or alternatively a calibration based on a thin film sample of known index, should improve the measurement.

The traditional method for extracting the thickness and refractive index of a thin film from spectrophotometer transmission scans of a thin film sample plate with a thin film layer, can be improved slightly by adding scans at angles that are different from normal incidence, and by adding reflection scans, but the accuracy of the results is still limited. If the substrate is a flat plate then the internal angle in the film layer is always less than the critical angle, and the gross spectral features such as peak positions are still determined by the product of the index and the thickness, and the extraction of the index and thickness separately depends on transmission or reflection levels that are more difficult to measure accurately.

For the device described herein, gross spectral features such as wavelength positions of peaks and dips depend on layer index and thickness independently in a more complex way, leading to more accurate extracted values. The more complex dependence on layer index and thickness is due to the dependence of the reflected phase on refractive index when the internal angle is beyond the critical angle.

Many companies and institutions working with thin film optics already have a spectrophotometer (or even many), which provides a light source and accurate wavelength selection. These spectrophotometers generally come with sophisticated software and interfaces for collecting and saving scan data. This apparatus can fit into an existing spectrophotometer, and the analysis software can simply read the standard spectrophotometer scan files and report the results, without having to interface directly with the spectrophotometer. One method of use that we described provides refractive index measurements over a wide wavelength range.

Although this invention has been described with respect to specific embodiments, it is not intended to be limited thereto and various modifications which will become apparent to the person of ordinary skill in the art are inted to fall within the spirit and scope of the invention as described herein taken in conjunction with the accompanying drawings and the appended claims.

I claim:

1. A device for measuring the thickness of a thin film that is on a sample plate, and the index of refraction of the material of said thin film as a function of wavelength, comprising:
    an input beam path having a direction of propagation,
    a first right prism consisting of a prism material that is transparent in the first wavelength band, the first right prism having:
        a first planar first transmission surface,
        a first planar first reflection surface, wherein the first planar first transmission surface and the first planar first reflection surface form a first prism angle that is acute,
        a first planar second transmission surface that is parallel to the first planar first transmission surface,
        a first planar second reflection surface that is parallel to the first planar first reflection surface,
    and a second right prism that is identical to the first right prism, having corresponding elements comprising:
        a second planar first transmission surface,
        a second planar first reflection surface,
        a second planar second transmission surface,
        a second planar second reflection surface, wherein
    the first right prism is mounted onto a first rotation stage, with the first rotation stage having a first rotation axis and a first rotational position about the first rotation axis with the first rotation axis in the first planar first transmission surface and also parallel to each of a line in the first planar first reflecting surface, a line in the first planar second reflecting surface, and a line in the first planar second transmitting surface
    the second right prism is mounted onto a second rotation stage, the second stage having a second rotation axis and a second rotational position about the second rotation axis, with the second rotation axis in the second planar second transmission surface, wherein the second rotation axis is also parallel to the first rotation axis, and also parallel to each of a line in the second planar first reflecting surface, a line in the second planar second reflecting surface, and a line in the second planar second transmitting surface
    the first rotation stage and the second rotation stage are positioned so that a light beam propagating with a central input axis is aligned and in the direction of the input beam path, will follow a light beam path, in which the light beam enters the first planar first transmission surface, then reflects from the first planar reflection surface at an angle of incidence, wherein the angle of incidence is greater than the critical angle for the prism material, then the light beam reflects from the first planar second reflection surface, then the light beam exits through the first planar second transmission surface, then the light beam enters the second right prism through the second planar second transmission surface, then the light beam reflects from the second planar second reflection surface, then the light beam reflects from the second planar first reflection surface, and then the light beam exits through the second planar first transmission surface in an output beam path that is aligned with the central input axis,
    and a means for pressing a thin film sample plate into close contact with the first planar first reflection surface.

2. A device according to claim 1 further comprising a polarizer placed in the light beam path.

3. A device according to claim 2 further comprising a first aperture placed in front of or behind the polarizer in the input beam path, and a second aperture placed behind the second right prism in the output beam path.

4. A device according to claim 3 wherein the second angular position is in mechanical relationship with the first angular position such that any change in the first angular position causes a change in the second rotational position that is equal to the change in the first angular position and is opposite in rotational direction to the change in the first angular position.

5. A device according to claim 4 further comprising a system to determine the first rotational position for which the first planar first transmission surface is perpendicular to the light beam, comprising a beam splitter, a retro-reflector, a focusing element, and a screen, in which the light beam is reflected by the beam splitter to form a reflected beam that is then reflected by the retro-reflector to form a retro-reflected beam that passes through the beam splitter, then the retro-reflected beam passes through the focusing element and onto the screen, and the light beam also passes through the beam splitter and is reflected from the first planar first transmission surface to form a first planar first transmission beam, that is reflected by the beam splitter to form a reflected beam of the first planar transmission beam, which then passes through the focusing element and onto the screen.

6. A device according to claim 3 further comprising a system to determine the first rotational position for which the first planar first transmission surface is perpendicular to the light beam, comprising a beam splitter, a retro-reflector, a focusing element, and a screen, in which the light beam is reflected by the beam splitter to form a reflected beam that is then reflected by the retro-reflector to form a retro-reflected beam that passes through the beam splitter, then the retro-reflected beam passes through the focusing element and onto the screen, and the light beam also passes through the beam splitter and is reflected from the first planar first transmission surface to form a first planar first transmission beam, that is reflected by the beam splitter to form a reflected beam of the first planar transmission beam, which then passes through the focusing element and onto the screen.

7. A device according to claim 2 wherein the second angular position is in mechanical relationship with the first angular position such that any change in the first angular position causes a change in the second rotational position that is equal to the change in the first angular position and is opposite in rotational direction to the change in the first angular position.

8. A device according to claim 7 further comprising a system to determine the first rotational position for which the first planar first transmission surface is perpendicular to the light beam, comprising a beam splitter, a retro-reflector, a focusing element, and a screen, in which the light beam is reflected by the beam splitter to form a reflected beam that is then reflected by the retro-reflector to form a retro-reflected beam that passes through the beam splitter, then the retro-reflected beam passes through the focusing element and onto the screen, and the light beam also passes through the beam splitter and is reflected from the first planar first transmission surface to form a first planar first transmission beam, that is reflected by the beam splitter to form a reflected beam of the first planar transmission beam, which then passes through the focusing element and onto the screen.

9. A device according to claim 2 further comprising a system to determine the first rotational position for which the first planar first transmission surface is perpendicular to the light beam, comprising a beam splitter, a retro-reflector, a focusing element, and a screen, in which the light beam is reflected by the beam splitter to form a reflected beam that is then reflected by the retro-reflector to form a retro-reflected beam that passes through the beam splitter, then the retro-reflected beam passes through the focusing element and onto the screen, and the light beam also passes through the beam splitter and is reflected from the first planar first transmission surface to form a first planar first transmission beam, that is reflected by the beam splitter to form a reflected beam of the first planar transmission beam, which then passes through the focusing element and onto the screen.

10. A device according to claim 1 further comprising a first aperture placed in front of or behind the polarizer in the input beam path, and a second aperture placed behind the second right prism in the output beam path.

11. A device according to claim 10 wherein the second angular position is in mechanical relationship with the first angular position such that any change in the first angular position causes a change in the second rotational position that is equal to the change in the first angular position and is opposite in rotational direction to the change in the first angular position.

12. A device according to claim 11 further comprising a system to determine the first rotational position for which the first planar first transmission surface is perpendicular to the light beam, comprising a beam splitter, a retro-reflector, a focusing element, and a screen, in which the light beam is reflected by the beam splitter to form a reflected beam that is then reflected by the retro-reflector to form a retro-reflected beam that passes through the beam splitter, then the retro-reflected beam passes through the focusing element and onto the screen, and the light beam also passes through the beam splitter and is reflected from the first planar first transmission surface to form a first planar first transmission beam, that is reflected by the beam splitter to form a reflected beam of the first planar transmission beam, which then passes through the focusing element and onto the screen.

13. A device according to claim 10 further comprising a system to determine the first rotational position for which the first planar first transmission surface is perpendicular to the light beam, comprising a beam splitter, a retro-reflector, a focusing element, and a screen, in which the light beam is reflected by the beam splitter to form a reflected beam that is then reflected by the retro-reflector to form a retro-reflected beam that passes through the beam splitter, then the retro-reflected beam passes through the focusing element and onto the screen, and the light beam also passes through the beam splitter and is reflected from the first planar first transmission surface to form a first planar first transmission beam, that is reflected by the beam splitter to form a reflected beam of the first planar transmission beam, which then passes through the focusing element and onto the screen.

14. A device according to claim 1 wherein the second angular position is in mechanical relationship with the first angular position such that any change in the first angular position causes a change in the second rotational position that is equal to the change in the first angular position and is opposite in rotational direction to the change in the first angular position.

15. A device according to claim 14 further comprising a system to determine the first rotational position for which the first planar first transmission surface is perpendicular to the light beam, comprising a beam splitter, a retro-reflector, a focusing element, and a screen, in which the light beam is reflected by the beam splitter to form a reflected beam that is then reflected by the retro-reflector to form a retro-reflected beam that passes through the beam splitter, then the retro-reflected beam passes through the focusing element and onto the screen, and the light beam also passes through the beam splitter and is reflected from the first planar first transmission surface to form a first planar first transmission beam, that is reflected by the beam splitter to form a reflected beam of the first planar transmission beam, which then passes through the focusing element and onto the screen.

16. A device according to claim 1 further comprising a system to determine the first rotational position for which the first planar first transmission surface is perpendicular to the light beam, comprising a beam splitter, a retro-reflector, a focusing element, and a screen, in which the light beam is reflected by the beam splitter to form a reflected beam that is then reflected by the retro-reflector to form a retro-reflected beam that passes through the beam splitter, then the retro-reflected beam passes through the focusing element and onto the screen, and the light beam also passes through the beam splitter and is reflected from the first planar first transmission surface to form a first planar first transmission beam, that is reflected by the beam splitter to form a reflected beam of the first planar transmission beam, which then passes through the focusing element and onto the screen.

* * * * *